United States Patent
Chapman (12)

(10) Patent No.: US 6,755,197 B2
(45) Date of Patent: *Jun. 29, 2004

(54) APPARATUS AND METHOD FOR SPIT AND BITE PROTECTION FROM DANGEROUS PERSONS

(75) Inventor: Bruce Chapman, Gardiner, NY (US)

(73) Assignee: Handle With Care, Inc., Gardiner, NY (US)

(*) Notice: Subject to any disclaimer, the term of this patent is extended or adjusted under 35 U.S.C. 154(b) by 0 days.

This patent is subject to a terminal disclaimer.

(21) Appl. No.: 10/023,534
(22) Filed: Dec. 18, 2001
(65) Prior Publication Data
US 2002/0053348 A1 May 9, 2002

Related U.S. Application Data

(63) Continuation-in-part of application No. 09/576,080, filed on May 20, 2000, now abandoned.

(51) Int. Cl.[7] .................................................. A61F 11/00
(52) U.S. Cl. .................... 128/857; 602/18; 128/DIG. 23
(58) Field of Search ................................. 128/846, 857, 128/858, DIG. 23; 602/17, 18; 2/9, 206; 5/630, 637

(56) References Cited

U.S. PATENT DOCUMENTS

| | | | | | |
|---|---|---|---|---|---|
| 4,017,906 A | * | 4/1977 | Bochynsky | ..................... | 2/10 |
| 4,291,417 A | * | 9/1981 | Pagano | ........................ | 2/202 |
| 5,214,804 A | * | 6/1993 | Carey | ........................... | 2/206 |
| 6,374,829 B1 | * | 4/2002 | Chapman | ..................... | 128/857 |

* cited by examiner

Primary Examiner—Michael A. Brown
(74) Attorney, Agent, or Firm—Edward Etkin, Esq.

(57) ABSTRACT

The inventive apparatus and method of use thereof remedies at least some of the problems and dangers associated with applying restraint holds to violent and/or struggling persons by protecting restraining or escorting personnel from harm that may be inflicted on them by the target person during and after application of restraint holds (such as spitting and biting). The inventive protective apparatus advantageously comprises an collar (for example a cervical collar) that protects and stabilizes the person's neck and prevents neck injuries and head-butting, and a readily deployable face shield that attaches to the cervical collar and that prevents the person from spitting on and/or biting the staff members. The face shield may be permanently or releasably attached to the collar.

16 Claims, 3 Drawing Sheets

APPARATUS AND METHOD FOR SPIT AND BITE PROTECTION FROM DANGEROUS PERSONS

REFERENCE TO PREVIOUSLY FILED APPLICATIONS

The present patent application is a continuation-in-part of a previously filed commonly assigned U.S. patent application Ser. No. 09/576,080, entitled "APPARATUS AND METHOD FOR PROVIDING HEAD, NECK, SPIT, AND BITE PROTECTION DURING AND SUBSEQUENT TO A RESTRAINING HOLD MAINTAINTED ON A PERSON" filed on May 20, 2000 now abandoned.

BACKGROUND OF THE INVENTION

The present invention is directed to a modular apparatus and method, utilized during application of a restraint hold by a group of persons to a target person, for providing spit and bite protection from the target person to the group applying the restraint hold and to all other persons coming on contact with the target person after application of the restraining hold.

There are many thousands of human service and law enforcement agencies and facilities that provide care and supervision to aggressive, suicidal, and emotionally disturbed persons (hereinafter commonly referred to as "EDPs"). The staff and officers (hereinafter commonly referred to as "staff members") working in these agencies regularly come into physical contact with the EDPs through the use of physical subduing or restraint holds when the EDP becomes aggressive. An example of an a safe and advantageous physical subduing hold is a Primary Restraint Technique (PRT) disclosed in commonly assigned U.S. Pat. No. 6,273,091, entitled "APPARATUS AND METHOD FOR SAFELY MAINTAINING A RESTRAINING HOLD ON A PERSON" Ser. No.: 09/442,709, filed Nov. 18, 1999.

During the process of application of a typical restraint hold, the EDP may violently shake their head—behavior that may result in neck and cervical spine damage. In addition, such behavior may pose a danger to the staff members escorting the EDP, as the EDP may attempt to head-butt the staff members. The second problem is that EDPs may attempt to spit at and/or bite the escorting staff members—a behavior that is particularly dangerous if the EDP is a carrier of an infectious disease such as AIDS, Hepatitis, and/or Tuberculosis.

Thus, it would be desirable to provide an apparatus and method to protect staff members from harm that may be inflicted on them by the EDP during and after application of restraint holds by the staff members.

SUMMARY OF THE INVENTION

The apparatus and method of use thereof of the present invention remedy some of the problems and dangers associated with applying restraint holds to violent and/or struggling EDPs in that they provide protection to the staff members from harm that may be inflicted on them by the EDP during and after application of restraint holds. In brief summary, the inventive modular apparatus advantageously provides: (1) an easily deployable cervical collar that protects and stabilizes the EDP's neck and prevents neck injuries and head-butting, and (2) a readily deployable face shield that attaches to the cervical collar and that prevents the EDP from spitting on and/or biting the staff members. Furthermore, the inventive apparatus may be readily deployed in any situation other than a restraint hold that requires application of a cervical collar and a spit and bite guard, such as for example during an epileptic seizure experienced by a medical patient.

The inventive protective apparatus comprises a cervical collar and a clear face shield that may be releasably attached to the cervical collar. To utilize the inventive apparatus the cervical collar is deployed first by placing the collar around the EDP's neck. The collar contains a releasable attachment mechanism, such as hook and loop material or snap-in buttons, that facilitates adjustable application of the collar to the EDP's neck. The face shield is then wrapped around the front portion of the EDP's head and releasably attached to the cervical collar (for example by hook and loop material, snap-in buttons, or the like) thus forming a transparent bite and spit guard. An alternate embodiment of the invention includes additional releasable means to secure the face shield to the collar.

Other objects and features of the present invention will become apparent from the following detailed description considered in conjunction with the accompanying drawings. It is to be understood, however, that the drawings are designed solely for purposes of illustration and not as a definition of the limits of the invention, for which reference should be made to the appended claims.

BRIEF DESCRIPTION OF THE DRAWINGS

In the drawings, wherein like reference characters denote corresponding or similar elements throughout the various figures.

DESCRIPTION OF THE PREFERRED EMBODIMENTS

The apparatus and method of use thereof of the present invention remedies some of the problems and dangers associated with escorting and applying restraint holds to violent and/or struggling EDPs by protecting the staff members from certain forms of harm that may be inflicted on them by the EDP during and after application of restraint holds and the escorting process.

It should be understood that while the present invention refers to Emotionally Disturbed Persons (hereinafter "EDPs") and Staff Members, the inventive techniques and apparatus may be applied in virtually any situation that requires application of a cervical collar and a spit and bite guard, such as for example during an epileptic seizure experienced by a medical patient or during application of a restraint hold to a violent and/or struggling EDP. Moreover, it should be understood that embodiments of the present invention described below and illustrated in FIGS. 1A to 5 are shown by way of example only such that relative sizes of various components, composition of materials, and releasable attachment devices of the inventive apparatus may be varied as a matter of design choice without departing from the spirit of the present invention.

Figure 1A:
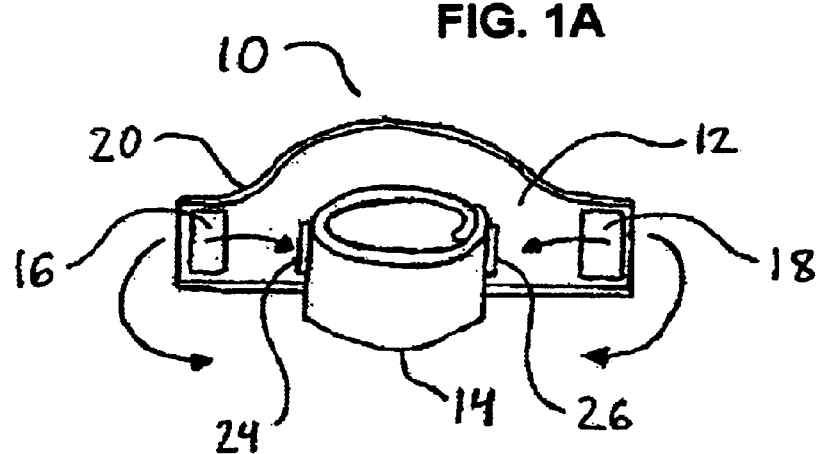
FIG. 1A shows a first embodiment of the protective apparatus of the present invention comprising a collar and a face shield.
Figure 1B:
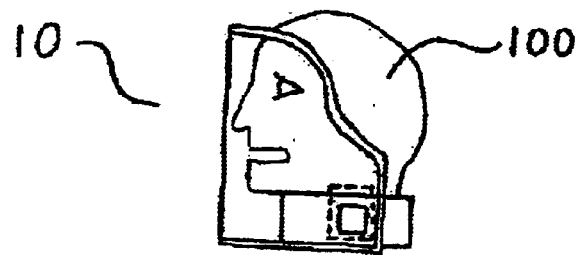
FIG. 1B shows a side view of the inventive protective apparatus of FIG. 1A.
Figure 1C:
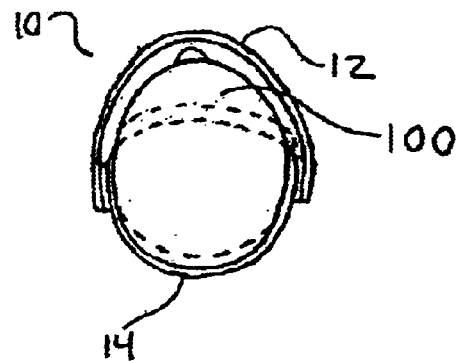
FIG. 1C shows a top view of the inventive protective apparatus of FIG. 1A.

Referring initially to FIGS. 1A–1C, a first embodiment of an inventive protective apparatus 10 is illustrated in a disassembled form. The protective apparatus 10 comprises two components: a face shield 12 and a collar 14. The face shield 12 preferably includes a shield 22 composed from a light flexible material such as flexible plastic. The plastic of the shield 22 may be clear, translucent or opaque as a matter of design choice. The face shield 12 preferably includes an outer border 20, for example, a plastic or rubber sheath along its edge such that the edge is dulled so as not to pose a danger of inflicting cuts on the EDP or staff members. The upper portion of the shield 22 may be generally outwardly curved to encompass all of the EDP's face when the face shield 12 is deployed. The face shield 12 also includes first releasable attachment devices 16, 18 disposed at respective left and right portions of the inner surface of the face shield 12 (i.e., the surface facing the EDP's face). The collar 14 may be any cervical collar composed of a rigid or a resilient material and may be provided as pre-sized or adjustable as a matter of design choice. Alternately, the collar 14 may simply serve as a collar to secure the face shield 12 to the EDP without having any cervical support. The collar 14 includes second releasable attachment devices 24, 26 disposed on opposing sides thereof. Thus, any existing cervical collar may be advantageously modified to serve as the collar 14 by securing releasable attachment devices 24, 26 to its opposing sides.

Preferably, the first releasable attachment devices 16, 18 and the corresponding second releasable attachment devices 24, 26 are sized and configured to releasably connect to one another to secure the face shield 12 to the collar 14 when the collar 14 is placed on the EDP (for example during or subsequent to a restraint hold) and the face shield 12 is placed and bent around, and in front of, the EDP's face. The specific releasable attachment devices 16, 18, 24, 26 utilized may be any known releasable attachment devices selected as a matter of design choice and may include, but are not limited to: hook and loop material, snap-in buttons, hole and hook devices, temporary glue pads, rectangular hole and twist bar, hole and button devices, etc. A side view of the protective apparatus 10 disposed on an EDP 100 is shown in FIG. 1B, while a top-down view of the apparatus 10 is shown in FIG. 1C. Optionally, the face shield 12 may be permanently secured to the collar 14 on one or both sides, such that when the collar 14 is applied to the EDP, the face shield does not need to be separately secured.

Figure 2:
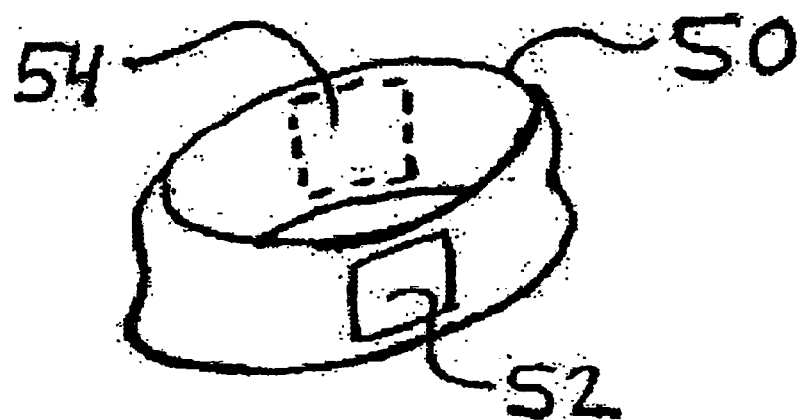
FIG. 2 shows a second exemplary embodiment of a collar component of the inventive protective apparatus of FIG. 1A.
Figure 3:
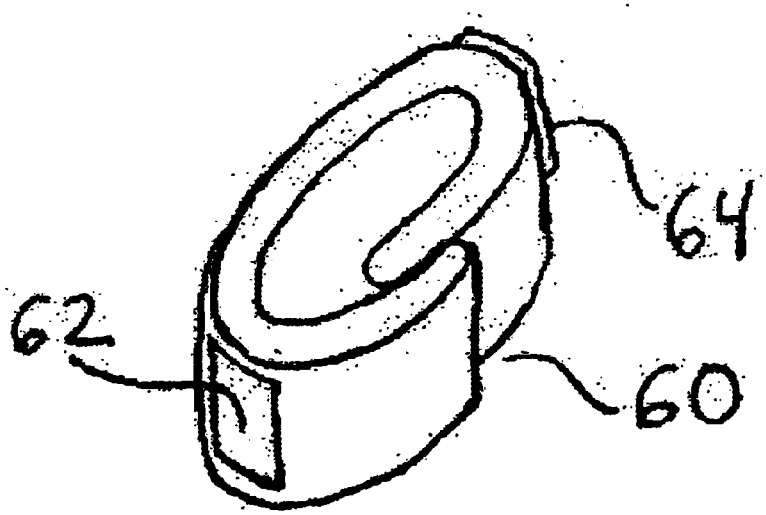
FIG. 3 shows a third exemplary embodiment of a collar component of the inventive protective apparatus of FIG. 1A.

Referring now to FIG. 2, the collar 14 is shown as a rigid collar 50 with releasable attachment devices 50, 52 disposed on its sides for attachment to the face shield 12 first releasable attachment devices 16, 18. Referring now to FIG. 3, the collar 14 is shown as a resilient adjustable flexible collar 60 that's wrapped around the EDP's neck. Preferably, releasable attachment devices 62, and 64, positioned on the outer surface of the flexible collar 60, are larger than releasable attachment devices 24, 26 so that when the collar is wrapped around the EDP's neck the devices 62, 64 are arranged to contact with the releasable attachment devices 16, 18, regardless of the size of the EDP's neck.

Figure 4:
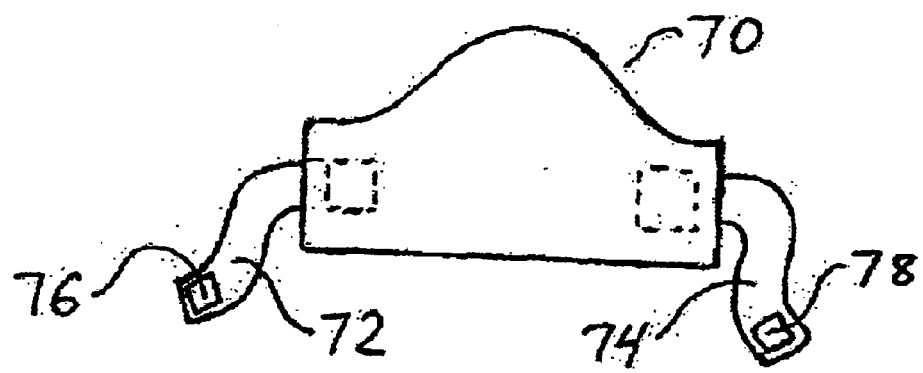
FIG. 4 shows a second exemplary embodiment of a face shield component of the inventive protective apparatus of FIG. 1A.
Figure 5:
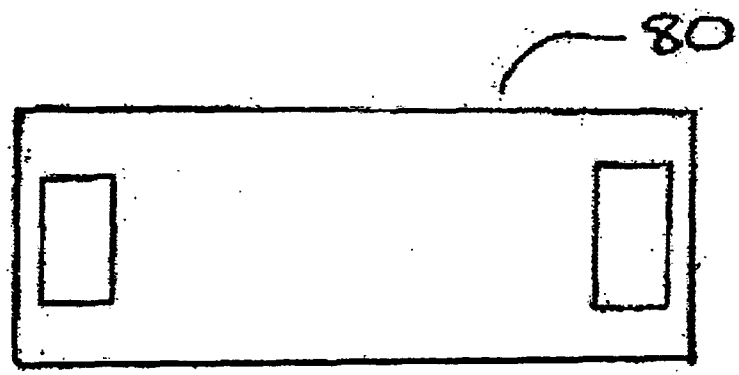
FIG. 5 shows a third exemplary embodiment of a face shield component of the inventive protective apparatus of FIG. 1A.

Referring now to FIG. 4, an alternate embodiment of the face shield 12 is shown as face shield 70 with flexible resilient straps 72, 74 attached to sides thereof. The straps 72, 74 include respective releasable attachment devices 76, 78 for releasable attachment to one another. The face shield 70 provides an additional measure to better secure it to the collar 14 for particularly violent or struggling EDPs—after the face shield 70 is secured to the collar 14, the straps 72, 74 are wrapped around the back of the EDP's head and secured to one another via the releasable attachment devices 76, 78. Optionally the straps 72, 74 may be replaced by a single flexible resilient strap attached to both ends of the face shield 70 (not shown). In this case, when the face shield 70 is applied to the collar 14, the single strap is positioned behind the EDP's head. Referring now to FIG. 5, an alternate embodiment of the face shield 12 is shown as a square face shield 80. As noted above, the exact shape of the face shield 12 is selected as a matter of design choice.

Thus, while there have shown and described and pointed out fundamental novel features of the invention as applied to preferred embodiments thereof, it will be understood that various omissions and substitutions and changes in the form and details of the devices and methods illustrated, and in their operation, may be made by those skilled in the art without departing from the spirit of the invention. For example, it is expressly intended that all combinations of those elements and/or method steps which perform substantially the same function in substantially the same way to achieve the same results are within the scope of the invention. It is the intention, therefore, to be limited only as indicated by the scope of the claims appended hereto.

I claim:

1. A protective apparatus for providing spit and bite protection from a restrained target person to all persons coming on contact with the target person, said apparatus comprising:

a collar, having a first side and a second side, positioned around the target person's neck;

a flexible face shield having an inner surface, a first end, a second end, and a protective region defined between said first end and said second end, said face shield being sized and configured to wrap around the target person's facial region;

first attachment means for attaching said face shield to said collar, by attaching said first end to said first side of said collar, and said second end to said second side of said collar, such that said face shield is wrapped around a front portion of the target person's head and said protective region is positioned in front of the target person's face thereby preventing the target person from spitting on or biting other persons.

2. The protective apparatus of claim 1, wherein said attachment means comprises first releasable attachment means for removably attaching said face shield to said collar when said face shield is wrapped around a front portion of the target person's head so that said inner surface contacts said first and second sides of said collar.

3. The protective apparatus of claim 2, wherein said first releasable attachment means comprises: a first pair of attachment devices disposed on said respective first and second sides of said collar; and a second pair of corresponding attachment devices, configured for releasable attachment to said first pair of attachment devices, positioned on said inner surface of said face shield such that when said face shield is wrapped around the target person's face, said first pair of attachment devices is placed into releasable contact with said second pair of attachment devices.

4. The protective apparatus of claim 3, wherein said first and second pairs of attachment devices are selected from at least one of: hook and loop material, snap-in buttons, hole and hook devices, hole and button devices, rectangular hole and twisting bar, and releasable glue pads.

5. The protective apparatus of claim 1, wherein said collar comprises one of: a flexible adjustable cervical collar composed of a substantially light and resilient material, and a rigid cervical collar.

6. The protective apparatus of claim 5, wherein said light resilient material is dense foam coated with a polyurethane compound.

7. The protective apparatus of claim 1, wherein said face shield further comprises a protective outer rim disposed around edges thereof for preventing cutting damage by said face shield.

8. The protective apparatus of claim 1, wherein said face shield is composed of flexible plastic.

9. The protective apparatus of claim 2, further comprising:

a pair of flexible resilient straps, a first strap attached to said first end of said face shield and a second strap attached to said second end of said face shield; and second releasable attachment means disposed on said pair of flexible straps for releasably attaching said straps to one another behind the target person's head after said face shield has been attached to said collar.

10. The protective apparatus of claim 2, further comprising:

a flexible resilient retaining strap having a first portion attached to said first end of said face shield and a second portion attached to said second end of said face shield, said retaining strap being positioned and configured to be moved behind the target person's head after said face shield has been attached to said collar.

11. The protective apparatus of claim 1, wherein said attachment means comprises:

secure attachment means for securing said first end of said face shield to said first side of said collar;

and third releasable attachment means for removably attaching said second end of said face shield to second side of said collar such that said face shield is wrapped around the target person's head and secured.

12. The protective apparatus of claim 11, wherein said third releasable attachment means comprises: a third releasable attachment device disposed on said second side of said collar; and a fourth corresponding releasable attachment device, configured for releasable attachment to said third attachment device, positioned on said inner surface of said face shield at said second end, such that when said face shield is wrapped around the target person's face, said third attachment device is placed into releasable contact with said fourth attachment device.

13. The protective apparatus of claim 12, wherein said third and fourth attachment devices are selected from at least one of: hook and loop material, snap-in buttons, hole and hook devices, hole and button devices, rectangular hole and twisting bar, and releasable glue pads.

14. A method for providing spit and bite protection from a restrained target person to all persons coming on contact with the target person, said method comprising the steps of:

(a) positioning a collar, having a first side and a second side, around the target person's neck; and (b) releasably attaching a flexible face shield to said collar such that said face shield is positioned in front of the target person's face thereby preventing the target person from spitting on or biting other persons.

15. The method of claim 14, wherein said collar comprises one of: a flexible adjustable cervical collar composed of a substantially light and resilient material, and a rigid cervical collar.

16. A method for providing spit and bite protection from a restrained target person to all persons coming on contact with the target person, said method comprising the steps of:

(a) modifying an existing cervical collar, having a first side and a second side, by securing releasable attachment devices to said first and second sides;

(b) positioning said collar around the target person's neck; and (c) releasably attaching a flexible face shield to said releasable attachment devices on said collar, such that said face shield is positioned in front of the target person's face thereby preventing the target person from spitting on or biting other persons.

\* \* \* \* \*